United States Patent [19]

Auer et al.

[11] Patent Number: 4,549,995

[45] Date of Patent: Oct. 29, 1985

[54] PROCESS FOR MAKING ALKANEPHOSPHONOUS ACID ESTERS

[75] Inventors: Eberhard Auer; Klaus Gehrmann; Alexander Ohorodnik, all of Erftstadt; Johannes Rosenthal, Cologne, all of Fed. Rep. of Germany

[73] Assignee: Hoechst Aktiengesellschaft, Fed. Rep. of Germany

[21] Appl. No.: 554,581

[22] Filed: Nov. 23, 1983

[30] Foreign Application Priority Data

Dec. 8, 1982 [DE] Fed. Rep. of Germany ....... 3245365

[51] Int. Cl.$^4$ ................................................. C07F 9/46
[52] U.S. Cl. ..................................... 260/973; 260/962
[58] Field of Search ..... 260/973, 962, 973 (U.S. only)

[56] References Cited

U.S. PATENT DOCUMENTS 2,722,538  11/1955  Jackson .............................. 260/973
2,903,475   9/1955  Harowitz ............................ 260/962

OTHER PUBLICATIONS

Arbuzov et al., "Chem. Abstracts", vol. 47, (1953), #9904c.

*Primary Examiner*—Anton H. Sutto
*Attorney, Agent, or Firm*—Connolly and Hutz

[57] ABSTRACT

The disclosure relates to an improved process for making alkanephosphonous acid esters which comprises: introducing a stoichiometric excess each of an alkyldihalogenophosphane and aliphatic alcohol into a reaction column and reacting them therein at a temperature higher than the boiling point of the reactants but lower than the boiling point of the resulting alkanephosphonous acid ester, this latter being obtained in the base portion of the reaction column and being removed therefrom; continuously expelling overhead of the reaction column a vaporous mixture consisting of by-products formed during the reaction, in the form of hydrogen halide and halide of the aliphatic alcohol, together with aliphatic alcohol in excess, and separating the mixture into its components in a series-connected distilling column, the aliphatic alcohol obtained in the base portion of the distilling column being removed therefrom and recycled into the reaction column, and selectively condensing the mixture issuing overhead with recovery of hydrogen halide gas and liquefied halide of the aliphatic alcohol.

4 Claims, 1 Drawing Figure

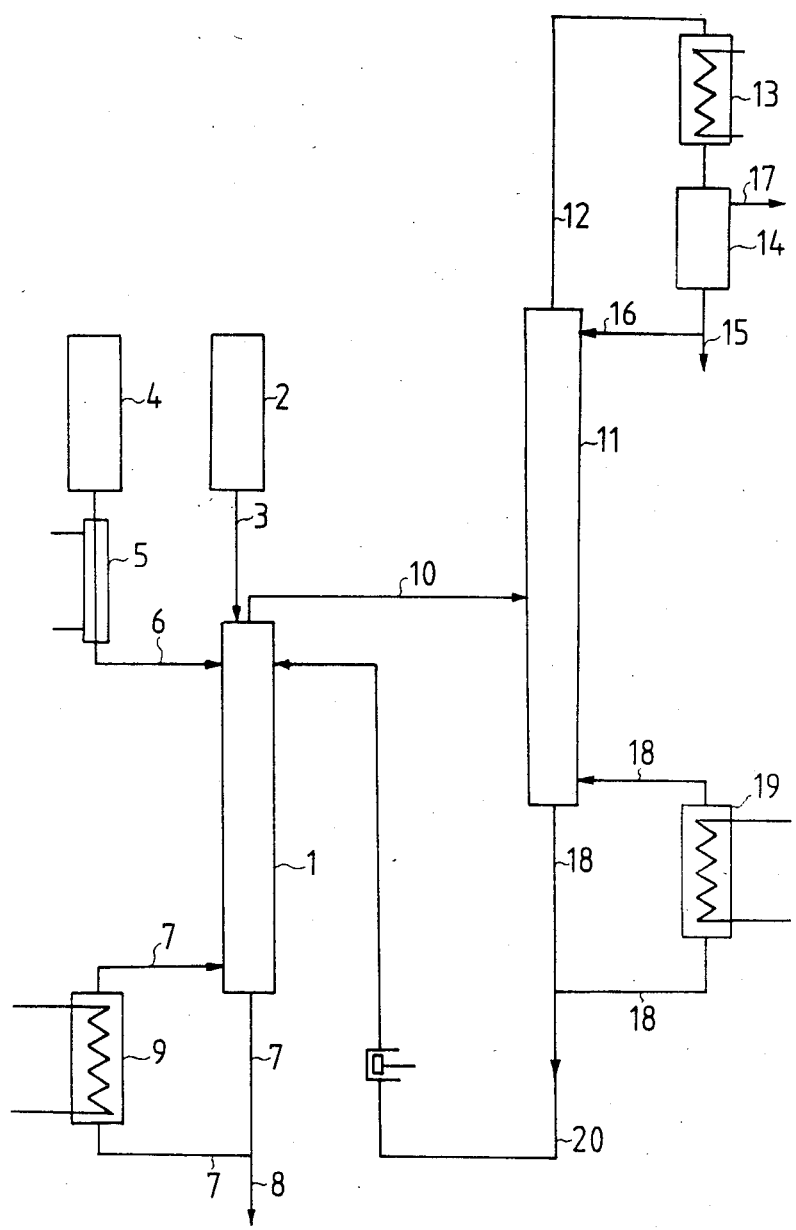

PROCESS FOR MAKING ALKANEPHOSPHONOUS ACID ESTERS

The present invention relates to an improved process for making alkanephosphonous acid esters by reacting an alkyldihalogenophosphane with an aliphatic alcohol, the final product being obtained in good yields and high purity.

Alkanephosphonous acid esters are of commercial interest which is basically due to their susceptibility of catalytically combining additively with double bonds while forming a wide variety of compounds which are widely used in the fields of plant protection and flameproofing materials. Vital to the use of these compounds in these fields is the purity of the feed materials employed for making them.

German Patent DE-PS No. 24 15 157 discloses a process for making alkanephosphonous acid esters by reacting an alkyldichlorophosphane with an aliphatic alcohol in accordance with the following equation 1

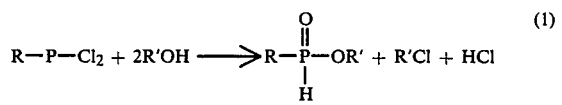
(1)

in which R and R' each stand for alkyl groups, wherein the alkyldichlorophosphane and aliphatic alcohol are heated to boiling in a reaction zone at temperatures of 50° to 200° C. in the presence of an inert gas selected from nitrogen, argon or carbon dioxide; resulting hydrogen halide and alcohol in excess distil over into the upper portion of the reaction zone, are condensed therein and removed therefrom, whilst the alkanephosphonous acid ester formed travels downwardly together with aliphatic alcohol in excess, if any, into the base portion of the reaction zone from which it is removed.

As a result of the fact that the hydrogen halide formed during the reaction just described is readily soluble in the aliphatic alcohol and also in the alkanephosphonous acid ester, the undesirable side reaction illustrated by the following equation 2 is liable to occur to some extent:

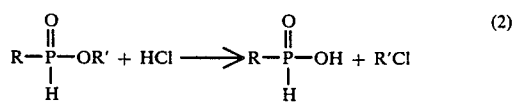
(2)

This side reaction has the following adverse effects:
(a) it reduces the yield of phosphonous acid ester;
(b) it entails the formation of alkanephosphonous acid which is required to be separated prior to subjecting the ester to further treatment;
(c) the alkanephosphonous acid decomposes at higher temperatures—quantitatively at 180° C.—into toxic and self-ignitable alkylphosphane and alkanephosphonic acid in accordance with the following equation 3:

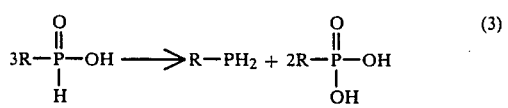
(3)

As a result, it is an imperative requirement to effect the distillative purification of the contaminated alkanephosphonous acid with extreme care.

The present process permits these adverse effects to be overcome or avoided by providing for the alkyldihalogenophosphane to be reacted with the aliphatic alcohol inside a bipartite reaction column, and for the hydrogen halide formed during the reaction column to be immediately removed together with aliphatic alcohol in excess, if any, from the reaction zone to avoid prolonged contact of the hydrogen halide with the phosphonous acid ester.

The present invention relates more particularly to a process for making alkanephosphonous acid esters of the following general formula I

(I)

in which x stands for an alkyl group having from 1 to 3 carbon atoms and y stands for an alkoxy group having from 4 to 6 carbon atoms, wherein an alkyldihalogenophosphane containing from 1 to 3 carbon atoms in the alkyl group is reacted with an aliphatic alcohol having from 4 to 6 carbon atoms at a temperature lower than the boiling point of the alkanephosphonous acid ester, and the components boiling at a lower temperature than the alkanephosphonous acid ester are distillatively separated from the reaction mixture, which comprises: introducing a stoichiometric excess each of the alkyldihalogenophosphane and aliphatic alcohol into a reaction column and reacting them therein at a temperature higher than the boiling point of the reactants but lower than the boiling point of the resulting alkanephosphonous acid ester, this latter being obtained in the base portion of the reaction column and being removed therefrom; continuously expelling overhead of the reaction column a vaporous mixture consisting of by-products formed during the reaction, in the form of hydrogen halide and halide of the aliphatic alcohol, together with aliphatic alcohol in excess, and separating the mixture into its components in a series-connected distilling column, the aliphatic alcohol obtained in the base portion of the distilling column being removed therefrom and recycled into the reaction column, and selectively condensing the mixture issuing overhead with recovery of hydrogen halide gas and liquefied halide of the aliphatic alcohol.

Further preferred and optional features of the present process provide:
(a) for the alkyldihalogenophosphane to be preheated to a temperature of about 40° to 85° C. prior to introducing it into the reaction column;
(b) for 2 to 10 times the necessary stoichiometric quantity of alcohol per mol alkyldihalogenophosphane to be introduced into the reaction column;
(c) for isobutanol to be used as the aliphatic alcohol and for reaction temperature to be 108° to 140° C.;
(d) for the present ester to be further purified and to this end for the alkanephosphonous acid ester obtained in the base portion of the reaction column to be removed therefrom, for it to be passed through a circulating evaporator, at a temperature of 150° to 200° C. and recycled into the base portion of the reaction column, and (e) for the base product obtained in the distilling column to be purified and to this end for the aliphatic alcohol obtained in the base portion of the distilling column to be removed therefrom, for it to be introduced into a circulating evaporator and freed therein at a temperature of 100° to 150° C. from contaminants boiling at a temperature lower than the aliphatic alcohol, and for the aliphatic alcohol so purified to be recycled into the reaction column.

In clear contrast with the prior art methods, the present process permits the hydrogen chloride formed during the reaction to be readily and completely separated from the alkanephosphonous acid esters so that the side reaction of equation 2 is no longer liable to take place, i.e. the ester obtained is free from alkanephosphonous acid and can be additively combined with C=C-double bonds, without it being necessary for it to be subjected to further treatment.

Alkanephosphonous acid esters which are free from alkanephosphonous acid are thermally stable and therefore easy to purify distillatively at temperatures of 180° C. or higher temperatures.

The beneficial effects of the present process are more fully described in the following Examples with reference to the accompanying drawing:

EXAMPLE 1

Methyldichlorophosphane and isobutanol as feed materials were continuously introduced into reaction column 1. The isobutanol came from a reservoir 2 and was introduced through line 3 at an hourly rate of 3.76 kg or 50.81 mols. The methyldichlorophosphane came from reservoir 4 and was introduced through preheater 5 and line 6 at an hourly rate of 2.64 kg or 22.56 mols. A temperature of 122° C. was found to establish in the reaction zone of reaction column 1.

Resulting methanephosphonous acid isobutyl ester was taken from reaction column 1 and introduced through cycle line 7 into circulating evaporator 9 maintained at 188° C., whilst a vapor mixture of isobutanol, isobutyl chloride and hydrogen chloride which issued at the head of reaction column 1 was introduced through line 10 into distilling column 11 in which liquid isobutanol was obtained as base product and isobutyl chloride and hydrogen chloride were obtained as head product, at a reflux ratio of 10:1. The head product which had a temperature of 68°-70° C. was removed through line 12, isobutyl chloride was liquefied in condenser 13 and introduced into reservoir 14 from which it was either taken through line 15 at an hourly rate of 2.32 kg or recycled through line 16 into distilling column 11, for reflux formation. Uncondensed hydrogen chloride gas was removed through line 17.

Isobutanol obtained in the base portion of distilling column 11 was recycled through line 18 and introduced into circulating evaporator 19 in which it was freed from residual hydrogen chloride gas. Next, it was re-pumped through line 20 into reaction column 1 at an hourly rate of 16-18 liters. 3.28 kg methanephosphonous acid isobutyl ester containing 93.3% ester was removed as crude product from reaction column 1 through line 8. The yield of pure ester was 99.7% of the theoretical. Less than 0.2 weight % was undistillable residue, based on the final product.

EXAMPLE 2 (Comparative Example)

An apparatus such as that described in Example 1 of German Patent DE-PS No. 24 15 757 was used. It consisted of a column 4 m long and 80 mm wide. After establishment of constant conditions, i.e. an evaporator temperature of 135° C. and a head temperature of 95° C., 2.64 kg/h methyldichlorophosphane and 5.93 kg/h isobutanol were reacted therein. 4.76 kg/h base product was taken from the evaporator. Gas-chromatographic analysis indicated that the product contained 62.5% methanephosphonous acid isobutyl ester. This corresponded to a yield of 97.1%.

Analysis of the distilled product indicated that it contained 1.4% undistillable residue.

EXAMPLE 3

The procedure was as in Example 1 but an equivalent quantity of ethyldichlorophosphane was substituted for the methyldichlorophosphane and reacted with isobutanol. 3.69 kg/h ethanephosphonous acid isobutylester of 91.2% strength (gas-chromatographic analysis) was obtained; this corresponded to a yield of 99.4% of the theoretical.

We claim:

1. In the process for making alkanephosphonous acid esters of the following general formula I

in which x stands for an alkyl group having from 1 to 3 carbon atoms and y stands for an alkoxy group having from 4 to 6 carbon atoms, wherein an alkyldihalogenophosphane containing from 1 to 3 carbon atoms in the alkyl group is reacted with an aliphatic alcohol having from 4 to 6 carbon atoms at a temperature lower than the boiling point of the alkanephosphonous acid ester, and the components boiling at a lower temperature than the alkanephosphonous acid ester are distillatively separated from the reaction mixture, the improvement which comprises: introducing a stoichiometric excess each of the alkyldihalogenophosphane and aliphatic alcohol into a reaction column and reacting them therein at a temperature higher than the boiling point of the reactants but lower than the boiling point of the resulting alkanephosphonous acid ester, this latter being obtained in the base portion of the reaction column and being removed therefrom; continuously expelling overhead of the reaction column a vaporous mixture consisting of by-products formed during the reaction, in the form of hydrogen halide and halide of the aliphatic alcohol, together with aliphatic alcohol in excess, and separating the mixture into its components in a series-connected distilling column, the aliphatic alcohol obtained in the base portion of the distilling column being removed therefrom and recycled into the reaction column, and selectively condensing the mixture issuing overhead with recovery of hydrogen halide gas and liquefied halide of the aliphatic alcohol.

2. The process as claimed in claim 1, wherein the alkyldihalogenophosphane is preheated to a temperature of about 40° to 85° C. prior to introducing it into the reaction column.

3. The process as claimed in claim 1, wherein 2 to 10 times the necessary stoichiometric quantity of alcohol per mol alkyldihalogenophosphane is introduced into the reaction column.

4. The process as claimed in claim 1, wherein isobutanol is used and the reaction temperature is 108° to 140° C.

* * * * *